(12) United States Patent
Hoyme et al.

(10) Patent No.: US 10,968,160 B2
(45) Date of Patent: Apr. 6, 2021

(54) SEPARATION OF PROPIONIC ACID FROM ACRYLIC ACID VIA AZEOTROPIC DISTILLATION

(71) Applicant: Eastman Chemical Company, Kingsport, TN (US)

(72) Inventors: Craig Alan Hoyme, Fall Branch, TN (US); Joseph Jerome Puhr, Kingsport, TN (US); Robert Sterling Kline, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/471,214

(22) PCT Filed: Dec. 15, 2017

(86) PCT No.: PCT/US2017/066761
§ 371 (c)(1),
(2) Date: Jun. 19, 2019

(87) PCT Pub. No.: WO2018/118700
PCT Pub. Date: Jun. 28, 2018

(65) Prior Publication Data
US 2020/0115312 A1  Apr. 16, 2020

Related U.S. Application Data

(60) Provisional application No. 62/437,713, filed on Dec. 22, 2016.

(51) Int. Cl.
*C07C 51/46* (2006.01)
(52) U.S. Cl.
CPC .................................. *C07C 51/46* (2013.01)
(58) Field of Classification Search
CPC ........................................................ C07C 51/46
See application file for complete search history.

(56) References Cited

U.S. PATENT DOCUMENTS

| | | | |
|---|---|---|---|
| 3,859,175 A * | 1/1975 | Ohrui | C07C 51/46 203/46 |
| 4,031,135 A * | 6/1977 | Engelbach | C07C 45/35 562/535 |
| 4,040,913 A | 8/1977 | Clovis et al. | |
| 4,147,885 A * | 4/1979 | Shimizu | C07C 45/35 562/535 |
| 4,365,087 A | 12/1982 | Kadowaki et al. | |
| 5,504,247 A | 4/1996 | Saxer | |
| 6,254,735 B1 | 7/2001 | Watzenberger | |
| 6,482,981 B2 | 11/2002 | Ueno et al. | |
| 7,612,231 B2 | 11/2009 | Kang et al. | |
| 8,308,913 B2 | 11/2012 | Kang et al. | |
| 8,440,859 B2 | 5/2013 | Dubois | |
| 8,658,823 B2 | 2/2014 | Peterson et al. | |
| 8,765,629 B2 | 7/2014 | Norman et al. | |
| 8,883,672 B2 | 11/2014 | Norman | |
| 8,932,434 B2 | 1/2015 | Lee et al. | |
| 8,993,801 B2 | 3/2015 | Boppana et al. | |
| 9,156,768 B2 | 10/2015 | Meier | |
| 9,193,661 B2 | 11/2015 | Peterson et al. | |
| 9,493,393 B2 | 11/2016 | Schultz et al. | |
| 9,504,934 B2 | 11/2016 | Agrawal et al. | |
| 2003/0143143 A1 * | 7/2003 | Matsumoto | B01D 53/38 423/245.3 |
| 2013/0118892 A1 | 5/2013 | Meier | |
| 2013/0317254 A1 | 11/2013 | Kotsianis et al. | |
| 2015/0119612 A1 | 4/2015 | Agrawal | |

FOREIGN PATENT DOCUMENTS

| | | |
|---|---|---|
| CN | 101 367 720 A | 2/2009 |
| DE | 33 02 525 A1 | 7/1984 |
| EP | 1 116 709 A1 | 7/2001 |
| EP | 1116709 A1 * | 7/2001 ............ C07C 57/04 |
| JP | H04 187657 A | 7/1992 |
| WO | WO 2013 155245 A2 | 1/2013 |
| WO | WO 2015 031182 A1 | 3/2015 |

OTHER PUBLICATIONS

Mostefa, Marie Le Page et al.; "Determination of the Solid-Liquid Phase Diagram of the Binary System Acrylic Acid + Propionic Acid"; Journal of Chemical & Engineering Data, vol. 57; 2012; pp. 1209-1212.
Olson, James D. et al; "Thermodynamics of Hydrogen-Bonding Mixtures. 5. GE, HE, and TSE and Zeotropy of Water + Acrylic Acid"; Ind. Eng. Chem. Res., vol. 47, No. 15; 2008, pp. 5127-5131.
Co-pending U. S. Appl. No. 16/471,233, filed Jun. 19, 2019; Craig Alan Hoyme, et al.
Notification of Transmittal of the International Search Report and the Written Opinion of the International Searching Authority, or the Declaration received in International Application No. PCT/US2017/066761 dated Mar. 5, 2018.
Notification of Transmittal of the International Search Report and the Written Opinion of the International Searching Authority, or the Declaration received in International Application No. PCT/US2017/066770 dated Mar. 6, 2018.
Bauer, William; "Acrylic Acid and Derivatives"; Kirk-Othmer Encyclopedia of Chemical Technology; 41 pages; Jun. 20, 2003; retrieved online through Wiley Online Library, accessed Sep. 11, 2020 (https://onlinelibrary.wiley.com/doi/full/10.002/0471238961.0103182502012105.a01).

* cited by examiner

*Primary Examiner* — Sikarl A Witherspoon
(74) *Attorney, Agent, or Firm* — Tammye L. Taylor Polk (57) ABSTRACT

The present disclosure relates to a process for producing high-purity acrylic acid using azeotropic distillation and using water as an entrainer. This disclosure provides a process for separating acrylic acid from recovered feed streams which comprise acrylic acid and saturated organic acids including propionic acid. The resulting acrylic acid product is of sufficient purity to produce acrylate esters and high molecular weight acrylic acid polymers.

20 Claims, 3 Drawing Sheets

SEPARATION OF PROPIONIC ACID FROM ACRYLIC ACID VIA AZEOTROPIC DISTILLATION

CROSS-REFERENCE TO RELATED APPLICATION(S)

This application is a national stage filing under 35 USC § 371 of International Application Number PCT/US2017/066761, filed on Dec. 15, 2017; which claims the benefit of the filing date to U.S. Provisional Application No. 62/437,713 filed on Dec. 22, 2016; the entire disclosures of which are incorporated by reference herein.

FIELD OF THE INVENTION

This present disclosure relates to a process for purifying acrylic acid using a water as an entrainer. More specifically, this disclosure relates to processes and apparatuses for the purification of acrylic acid from a saturated organic acid stream comprising propionic acid using azeotropic distillation and water as an entrainer.

BACKGROUND OF THE INVENTION

Purified acrylic acid (prop-2-enoic acid) is a basic building block for the production of acrylate esters and superabsorbent polymers. Superabsorbent polymers are used in applications such as disposable diapers, ion exchange resins, adhesives, detergents, and thickening agents for pharmaceuticals, cosmetics, and paints. Reaction impurities must be separated from acrylic acid to enable the production of these high molecular weight acrylic acid polymers.

During the production of acrylic acid, reaction by-products are formed that must be separated from the acrylic acid to enable the production of the acrylate esters and superabsorbent polymers. The purification of acrylic acid to glacial acrylic acid typically requires the separation of acrylic acid from mixtures comprising propionic acid or mixtures comprising acetic acid. For acrylic acid mixtures comprising propionic acid, it is difficult to separate acrylic acid from propionic acid using conventional distillation due to their close boiling points (the boiling point of acrylic acid is 142.0° C., and the boiling point of propionic acid is 140.9° C.). Unfortunately, propionic acid is a by-product found in most acrylic acid processes including, but not limited to, propylene oxidation, the condensation of formaldehyde and acetic acid, and the bio-based production of acrylic acid from glycerol.

This present disclosure provides a process to separate and purify a chemical mixture comprising acrylic acid and propionic acid using azeotropic distillation with water as an entrainer to produce an acrylic acid product of sufficient purity to produce high molecular weight acrylic acid polymers.

SUMMARY OF THE INVENTION

One embodiment of the present disclosure comprises a process for purifying acrylic acid comprising:

supplying a feed stream to an azeotropic distillation column, wherein the feed stream comprises water, acrylic acid, and at least one saturated organic acid with 3 or more carbon atoms; and adding water as an entrainer to the azeotropic distillation column, such that the feed stream is separated into at least a product top stream and a product bottom stream, wherein the product top stream comprises the saturated organic acid and water and wherein the product bottom stream comprises the acrylic acid and optionally acetic acid.

One embodiment of the present disclosure comprises a process for purifying acrylic acid comprising:

supplying a feed stream to an azeotropic distillation column, wherein the feed stream comprises water, acrylic acid, and propionic acid; and adding water as an entrainer to the azeotropic distillation column, at a temperature and pressure such that the feed stream is separated into at least a product top stream and a product bottom stream, wherein the product top stream comprises propionic acid and water and wherein the product bottom stream comprises the acrylic acid.

One embodiment of the present disclosure comprises a process for purifying acrylic acid comprising:

supplying a first feed stream to a first azeotropic distillation column, wherein the first feed stream comprises water, acrylic acid, propionic acid, acetic acid, and high boiling compounds and adding water as an entrainer to the azeotropic distillation column, such that the first feed stream is separated into at least a first product top stream and a first product bottom stream, wherein the first product top stream comprises propionic acid, water and other compounds forming a minimum boiling azeotrope with water and wherein the first product bottom stream comprises the acrylic acid and acetic acid;

feeding the first product bottom stream of water, acrylic acid and acetic acid into a second distillation column to form a second top product stream comprising water and acetic acid and a second product bottom stream comprising acrylic acid and high boiling compounds with an optional second product side stream comprising concentrated acetic acid; and feeding the second product bottom stream of acrylic acid and high boiling compounds into a third distillation column to form a third product top stream comprising acrylic acid and a third product bottom stream comprising the remaining high boiling compounds.

One embodiment of the present disclosure comprises a process for purifying acrylic acid comprising supplying a first feed stream to a first distillation column, wherein the first feed stream comprises water, acrylic acid, propionic acid, acetic acid, and high boiling compounds to form a first product top stream comprising acetic acid and water and a first product bottom stream comprising acrylic acid and propionic acid with an optional product side stream comprising concentrated acetic acid;

feeding said first product bottom stream comprising acrylic acid and propionic acid into an azeotropic distillation column, and adding water as an entrainer to the azeotropic distillation column, such that the second feed stream is separated into at least a second product top stream and a second product bottom stream, wherein the second product top stream comprises water, propionic acid, and other compounds forming a minimum boiling azeotrope with water and wherein the second product bottom stream comprises the acrylic acid and high boiling compounds; and feeding the second product bottom stream of acrylic acid and high boiling compounds into a second distillation column to form a third top product stream comprising acrylic acid and a third product bottom stream comprising high boiling compounds.

One embodiment of the present disclosure comprises a process for purifying acrylic acid comprising:

supplying a first feed stream to a first distillation column, wherein the first feed stream comprises water, acrylic acid, propionic acid, acetic acid, and high boiling compounds to form a first product top stream comprising acetic acid and water and a first product bottom stream comprising acrylic acid and propionic acid with an optional product side stream comprising concentrated acetic acid;

feeding said first product bottom stream comprising acrylic acid and propionic acid into a second distillation column, such that the second feed stream is separated into at least a second product top stream and a second product bottom stream, wherein the second product top stream comprises water, acrylic acid and propionic acid and wherein the second product bottom stream comprises the acrylic acid and high boiling compounds;

feeding said second product top stream comprising water, acrylic acid and propionic acid into an azeotropic distillation column, and adding water as an entrainer to the azeotropic distillation column, such that the feed stream is separated into at least a third product top stream and a third product bottom stream, wherein the third product top stream comprises water, propionic acid, and other compounds forming a minimum boiling azeotrope with water and wherein the third product bottom stream comprises the acrylic acid and high boiling compounds; and feeding said second product bottom stream of acrylic acid and high boiling compounds into a third distillation column to form a fourth product top product stream comprising acrylic acid and a fourth product bottom stream comprising high boiling compounds; or combining the third product bottom stream of acrylic acid and high boiling compounds with the second product bottom stream of acrylic acid and high boiling compounds and feeding this combined stream into a third distillation column to form a fourth product top product stream comprising acrylic acid which can be optionally combined with the acrylic acid from the second product bottom stream and a fourth product bottom stream comprising high boiling compounds.

One embodiment of the present disclosure comprises a process for purifying acrylic acid comprising:

supplying a first feed stream to a reactor, wherein the first feed stream comprises water, acrylic acid, acrylic acid oligomers, acetic acid, and propionic acid, wherein the acrylic acid dimers and the feed stream is heated and cracked back to acrylic acid; and feeding the cracked vapor stream from the reactor to a first azeotropic distillation column and adding water as an entrainer to form a product top stream comprising water, propionic acid, and other compounds forming minimum boiling azeotropes with water and a product bottom stream comprising acrylic acid.

One embodiment of the present disclosure comprises a process for purifying acrylic acid comprising:

supplying a first feed stream to a reactor, wherein the first feed stream comprises water, acrylic acid, acrylic acid oligomers, acetic acid, propionic acid, furfural, and maleic acid and the feed stream is heated and cracked back to acrylic acid; and feeding the cracked vapor stream from the reactor to a first azeotropic distillation column and adding water as an entrainer to form a product top stream comprising water, propionic acid, furfural and other compounds forming minimum boiling azeotropes with water and a product bottom stream comprising acrylic acid.

DETAILED DESCRIPTION

The purification of acrylic acid from reaction by-products is an energy and capital intensive operation. To produce superabsorbent polymers, the acrylic acid product must meet stringent product specifications. Typically, for superabsorbent polymers, the total aldehydes must be less than 10 ppm, the total saturated acids are less than 1600 ppm, acetic acid is less than 500-1500 ppm, propionic acid is less than 100-500 ppm. To obtain these specifications, many separation steps are required, and they can include multiple unit operations such as distillation, extraction, and/or crystallization.

Acrylic acid can be produced from many different starting materials and routes. In one embodiment of the present disclosure, the route is the oxidation of propylene to acrylic acid. In another embodiment, the route is from the reaction of formaldehyde and acetic acid. Bio-based routes are also suitable in the present disclosure to produce acrylic acid. These processes have some similar separation challenges, but also have unique separation issues that can result in a process that is both energy and capital intensive.

The purification of acrylic acid from mixtures comprising propionic acid is difficult using conventional distillation because acrylic acid and propionic acid are close boiling in nature and form a minimum boiling homogeneous azeotrope (the boiling point of acrylic acid is 142.0° C., the boiling point of propionic acid is 140.9° C., and the boiling point of the minimum boiling azeotrope is 140.2° C.). Due to the formation of the minimum boiling azeotrope, it is not possible to completely separate propionic acid from acrylic acid and recover the vast majority of the desired acrylic acid product in a highly refined state using just conventional distillation.

One aspect of the present disclosure enables the separation of propionic acid from acrylic acid by applying azeotropic distillation using water as the entrainer. Water forms a minimum boiling azeotrope with propionic acid but does not form an azeotrope with acrylic acid. In one aspect of the invention, the addition of the appropriate amount of water to a distillation column with a feed stream comprising acrylic acid and propionic acid will separate propionic acid from the acrylic acid with propionic acid and water as the column distillate top product and acrylic acid as the column bottoms product. In one embodiment, this separation can also be accomplished with a feed stream comprising acetic acid.

Figure 1:
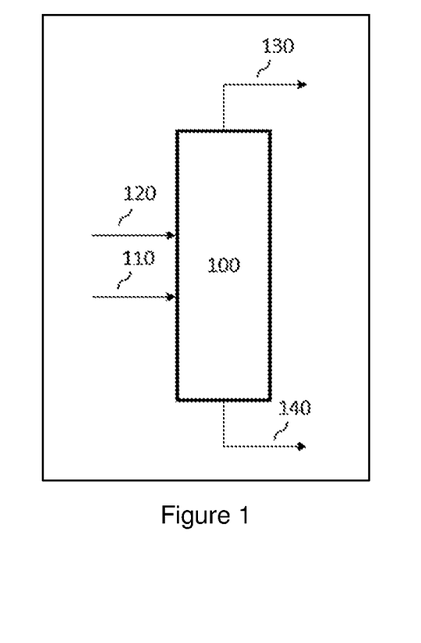
FIG. 1 illustrates an azeotropic distillation column of the present disclosure.

Some embodiments of the present invention, as shown in FIG. 1, provide a process for purifying acrylic acid comprising: supplying a feed stream 110 to an azeotropic distillation column 100. In some embodiments, the column may have one or more condensers, and in some embodiments, the column may have one or more reboilers. In some embodiments, the column does not have condensers, and in some embodiments, the column does not have reboilers. In some embodiments, the feed stream 110 comprises water, acrylic acid, and at least one saturated organic acid with 3 or more carbon atoms; adding an entrainer 120 consisting essentially of water wherein the water that acts as an entrainer and azeotroping agent in the azeotropic distillation column 100, at a temperature and pressure such that the feed stream is separated into at least a product top stream 130 and a product bottom stream 140, wherein the product top stream 130 comprises the saturated organic acid and water, and wherein the product bottom stream 140 comprises the acrylic acid.

In one aspect of the present invention, the feed stream 110 is recovered from the production of acrylic acid by propylene oxidation, wherein said feed stream comprises acrylic acid, acetic acid, propionic acid, water, and high boiling by-products. For example, such processes are described in U.S. Pat. Nos. 4,031,135, 4,147,885, and 4,365,087 which are herein incorporated by reference.

In another aspect of the present invention, the feed stream 110 is recovered from the production of acrylic acid by an aldolization reaction, wherein said feed stream comprises acrylic acid, acetic acid, propionic acid, water, and high boiling by-products. For example, such processes are described in U.S. Pat. Nos. 8,765,629 and 8,883,672 which are herein incorporated by reference.

In another aspect of the present disclosure, the feed stream 110 is recovered from the production of acrylic acid from alternative or bio-based routes such as propane oxidation, 3-hydroxypropionic acid, glycerol, and lactic acid wherein said feed stream comprises acrylic acid, acetic acid, propionic acid, water, and high boiling by-products. For example, such processes are described and referenced in U.S. Pat. No. 9,493,393 which is herein incorporated by reference.

Another embodiment of the present disclosure is for the separation of propionic acid from acrylic acid using an azeotropic distillation with water as the entrainer. The acrylic acid can come from a variety of processes including, but not limited to propylene oxidation, the condensation of formaldehyde and acetic acid, and the production of bio-based acrylic acid from glycerol. The feed composition for one embodiment comprises acrylic acid greater than 10 wt % (in another embodiment, the acrylic acid concentration is greater than 20 wt %), and a propionic acid concentration of less than 5 wt % (in another embodiment, the propionic acid concentration is less than 1 wt %).

Another embodiment of the present disclosure, provides a process for purifying acrylic acid comprising: supplying a feed stream to an azeotropic distillation column, wherein the feed stream comprises water, acrylic acid, acetic acid, and at least one saturated organic acid with 3 or more carbon atoms; using water as an entrainer in the azeotropic distillation column, at a temperature and pressure such that the feed stream is separated into at least a product top stream and a product bottom stream, wherein the product top stream comprises the saturated organic acid and water and wherein the product bottom stream comprises the acetic acid and acrylic acid.

Another embodiment of the present invention, provides a process for purifying acrylic acid comprising: supplying a feed stream to an azeotropic distillation column, wherein the feed stream comprises water, acrylic acid, and propionic acid; using water as an entrainer in the azeotropic distillation column, at a temperature and pressure such that the feed stream is separated into at least a product top stream and a product bottom stream, wherein the product top stream comprises propionic acid and water and wherein the product bottom stream comprises the acrylic acid.

In general, acrylic acid has a strong tendency to polymerize, so in some embodiments a stabilizing polymerization inhibitor is added to the process. Any acrylic acid polymerization inhibitor is suitable for use in the processes of the present disclosure. For example, in some embodiments, any acrylic acid polymerization inhibitor that doesn't azeotrope with water is suitable for use in this process. In some embodiments, suitable polymerization inhibitors may form minimum boiling azeotropes with water. In these embodiments, the polymerization inhibitors should be fed into the column in a place where water concentration is very low, the acrylic acid concentration is fairly high, or the column temperature is high enough to enable acrylic acid polymerization. For example, in some embodiments, the polymerization inhibitors are fed into the column towards the bottom of the column or into the column reboiler. In one embodiment, the polymerization inhibitors are selected from diphenylamine or its derivatives, phenothiazine, p-methoxyphenol, hydroquinone or hydroquinone monomethylether, nitroso compounds such as 2-methyl-2-nitrosopropane, nitrosobenzene, and 4-nitrosophenol.

In some embodiments, the product top stream from the azeotropic distillation column further comprises other organic compounds that form minimum boiling azeotropes with water such as furfural, benzaldehyde, and toluene. In one embodiment, the product top stream contains at least 90% of the propionic acid in the feed stream. In another embodiment, the product top stream contains at least 95% of the propionic acid in the feed stream. In another embodiment, the product top stream contains at least 99% of the propionic acid in the feed stream. In another embodiment, the product top stream contains at least 99.5% of the propionic acid in the feed stream. In another embodiment, the product top stream contains at least 99.7% of the propionic acid in the feed stream. In one embodiment, the acrylic acid present in the product bottom stream is at a higher concentration than in the feed stream.

In one embodiment, the azeotropic distillation operates at a pressure less than or equal to 1000 torr. In one embodiment, the azeotropic distillation operates at a maximum temperature from about 110° C. to about 150° C. or from about 120° C. to about 140° C. where the acrylic acid concentration is greater than 35 wt %; for example, at temperatures less than about 150° C., or at a temperature less than about 140° C., or at temperature less than about 130° C., or at a temperature less than about 120° C., or at a temperature less than about 115° C. where the acrylic acid concentration is greater than 35 wt %.

In one aspect of the present invention, the azeotropic distillation columns 100 may be operated at any suitable conditions for acrylic acid purification. In some embodiments, it must be operated at temperatures, pressures and residence times to enable the water to act as an entrainer and minimize the oligomerization of acrylic acid. In some embodiments, the temperature profile of the distillation column is lowest at the top of the column and highest at the bottom of the column. Therefore, in order to minimize the oligomerization of acrylic acid, in one embodiment, the temperature of the column should be controlled to temperatures less than 115-150° C. where the acrylic acid concentration is greater than 35 wt %. In one embodiment of the present disclosure, the column temperature is controlled to temperatures of 115° C. to 150° C. where the acrylic acid concentration is greater than 35 wt %. In one embodiment of the present disclosure, the column temperature is controlled to less than 150° C. where the acrylic acid concentration is greater than 35 wt %. In one embodiment of the present disclosure, the column temperature is controlled to less than 140° C. where the acrylic acid concentration is greater than 35 wt %. In one embodiment of the present disclosure, the column temperature is controlled to less than 135° C. where the acrylic acid concentration is greater than 35 wt %. In another embodiment, the column temperature is controlled to less than 130° C. where the acrylic acid concentration is greater than 35 wt %. In one embodiment of the present disclosure, the column temperature is controlled to less than 125° C. where the acrylic acid concentration is greater than 35 wt %. In another embodiment, the column temperature is controlled to less than 120° C. where the acrylic acid concentration is greater than 35 wt %. In another embodiment, the column temperature is controlled to less than 115° C. where the acrylic acid concentration is greater than 35 wt %. In some embodiments, the column operates at a pressure less than or equal to 1000 torr.

In some embodiments of the present invention, the acrylic acid concentrates below the feed, and is therefore most concentrated at the bottom of the column and the temperatures should be controlled below the feed or towards the bottom of the column or in the reboiler.

Another aspect of the present disclosure provides a process for purifying acrylic acid comprising: supplying a feed stream comprising water, acetic acid, acrylic acid, propionic acid, and high boiling by-products to a first separation column to produce a product top stream comprising acetic acid and water and a product bottom stream comprising crude acrylic acid, propionic acid, and high boiling by-products and optionally providing a product side-draw near the top of the column to produce a concentrated acid side-stream comprising acetic acid; supplying the product bottom stream from the first separation column to a second separation column to produce a product top stream comprising acrylic acid and propionic acid and a product bottom stream comprising the acrylic acid and high boiling by-products; supplying the product top stream from the second separation column to an azeotropic distillation column and using water as an entrainer to produce a product top stream comprising water and propionic acid and a product bottom stream comprising acrylic acid; and supplying the acrylic acid and high boiling by-product bottom stream from the second separation column and the acrylic acid bottom stream from the azeotropic distillation column to a third separation column to produce a product top stream comprising acrylic acid and a product bottom stream comprising high boiling by-products.

Another aspect of the present disclosure provides a process for purifying acrylic acid comprising: supplying a high boiler feed stream comprising acrylic acid, acrylic acid oligomers, propionic acid, furfural and impurities with a boiling point equal to or higher than acrylic acid to a reactor to pyrolize the acrylic acid oligomers to acrylic acid and produce an intermediate product stream comprising acrylic acid, acrylic acid oligomers, propionic acid, furfural and reaction by-products; and supplying the intermediate product stream to an azeotropic distillation column and using water as an entrainer operated at a temperature and pressure to form a product top stream comprising water, propionic acid, low boiling by-products, and other organic compounds forming minimum boiling azeotropes with water such as furfural, benzaldehyde, and toluene and a product bottom stream comprising the acrylic acid and high boiling by-products.

The recovery of propionic acid, other C3+ saturated organic acids (C3+ means a saturated organic acid with has 3 or more carbon atoms), and other organic compounds forming minimum boiling azeotropes with water is enabled by the use of water as an entrainer. Water forms minimum boiling azeotropes with C3+ saturated organic acids which are lower boiling than acrylic acid and lower boiling than any acrylic acid/C3+ saturated organic acid azeotropes. This enables water to remove the C3+ saturated organic acids in a distillation column as long as enough water is added to the column and if the column is operated appropriately. The amount of water required for the separation is typically determined by the feed composition, desired saturated organic acid recovery and column operation parameters such as distillate to feed ratio, reflux ratio, and other typically controlled column parameters. In one aspect of the present invention, the amount of water in the azeotropic distillation column may be any amount suitable to enable the water to act as an entrainer. Depending on the column operation and desired recoveries, the necessary water to feed ratio (wt/wt) may be greater than or equal to 1.0. In one embodiment, the water to feed ratio in the azeotropic distillation is greater than 1.2. In another embodiment, the water to feed ratio is greater than 1.3. In another embodiment, the water to feed ratio is greater than 1.4. In another embodiment, the water to feed ratio is greater than 1.5. In some embodiments, the water to feed ratio in the azeotropic distillation is 1.5 to 4 or 1.5 to 3 or 1.5 to 2.

In some embodiments, the feed stream comprises 1-80 wt % acrylic acid, 0-80 wt % acetic acid, and 0-60 wt % additional components where the total composition does not exceed 100 wt %. In some embodiments, the feed stream comprises 1-80 wt % acrylic acid, 1-80 wt % acetic acid, and 1-60 wt % additional components where the total composition does not exceed 100 wt %. In one embodiment, the feed stream comprises 5-25 wt % acrylic acid, 50-80 wt % acetic acid, 5-20 wt % water, and 0.001-0.3 wt % propionic acid. In one embodiment, the feed stream comprises 5-50 wt % acrylic acid, 50-80 wt % acetic acid, 0.1-20 wt % water, and 0.05-1 wt % propionic acid. In another embodiment, the feed stream comprises 50-80 wt % acrylic acid, 10-20 wt % acetic acid, 3-10 wt % water, and 0.001-0.3 wt % propionic acid. In another embodiment, the feed stream comprises 60-80 wt % acrylic acid, 0.01-5 wt % acetic acid, 0.01-5 wt % water, and 0.01-5 wt % propionic acid. In another embodiment, the feed stream comprises 50-80 wt % acrylic acid, 0.1-20 wt % acetic acid, 0.1-10 wt % water, and 0.001-0.5 wt % propionic acid. In some embodiments, the feed stream comprises less than 80 wt % acrylic acid. In some embodiments, the additional components comprise by-products from the initial reaction to produce acrylic acid and they may comprise high boiling, lower boiling or intermediate boiling components such as propionic acid, furfural, benzaldehyde, maleic acid, toluene, or other impurities. In one embodiment, the total amount of the additional components is less than 5 wt %; particularly in embodiments when the feed stream is from an intermediate stream coming directly from the initial reaction to produce acrylic acid followed by some additional distillation steps. In other embodiments, the total amount of additional components can be much greater than 5 wt % when the feed stream comes from a distillation high-boiler purge or from a melt crystallization purge stream in which they are separated and concentrated from the acrylic acid in the intermediate stream.

Additionally, in some embodiments, this present disclosure enables the separation of other components in the feed which form minimum boiling azeotropes with water (aldehydes with 3 or more carbon atoms, saturated carboxylic acids with 3 or more carbon atoms, alcohols with 2 or more carbon atoms, alkanes, aromatics, esters, and ketones with 4 or more carbon atoms). If the appropriate amount of water is present in the column, these components will concentrate in the distillate product with the water and the acrylic acid concentrating in the bottoms product of the azeotropic distillation column. It is important to remove these components along with propionic acid to low concentrations in order for the resulting acrylic acid product to be used as a feed for the production of high molecular weight acrylic acid polymers like superabsorbent polymers (SAPs).

For glacial acrylic acid, the maximum concentrations of impurities are as follows: for propionic acid, the concentration is limited to 100 ppm or less; for aldehydes, the total aldehyde concentration is limited to 10 ppm or less; for saturated organic acids, the concentration is limited to 1600 pm or less; for acetic acid, the concentration is limited to less than 500-1500 ppm.

In one aspect of the present disclosure, the product side stream comprises glacial or high purity acrylic acid. In some embodiments, the high purity acrylic acid comprises a total aldehydes concentration of less than 10 ppm, the total saturated acid concentration is less than 1600 ppm, the acetic acid concentration is less than 500-1500 ppm, and the propionic acid concentration is less than 100-500 ppm. In some embodiments, the high purity acrylic acid comprises an acetic acid concentration less than 500 ppm, and a propionic acid concentration less than 100 ppm. In some embodiments, the high purity acrylic acid comprises an acetic acid concentration less than 500 ppm.

One embodiment of the present disclosure is to remove propionic acid and other compounds from an intermediate acrylic acid product produced from the reaction of acetic acid and formaldehyde.

Another embodiment of the present disclosure is to remove propionic acid and other compounds from an acrylic acid stream.

Another embodiment of the present disclosure is to remove propionic acid and other compounds from a concentrated impurity purge stream produced during the purification of acrylic acid.

During the production of acrylic acid from acetic acid and formaldehyde, propionic acid and other components are produced at low, but not inconsequential concentrations. The purification of the desired acrylic acid generates an intermediate acrylic acid product stream comprising acrylic acid, propionic acid, acetic acid, and other reaction impurities. Using water as an entrainer in an azeotropic distillation column will result in the separation of propionic acid and other components which form minimum boiling azeotropes with water from the desired acrylic acid product.

Figure 2:
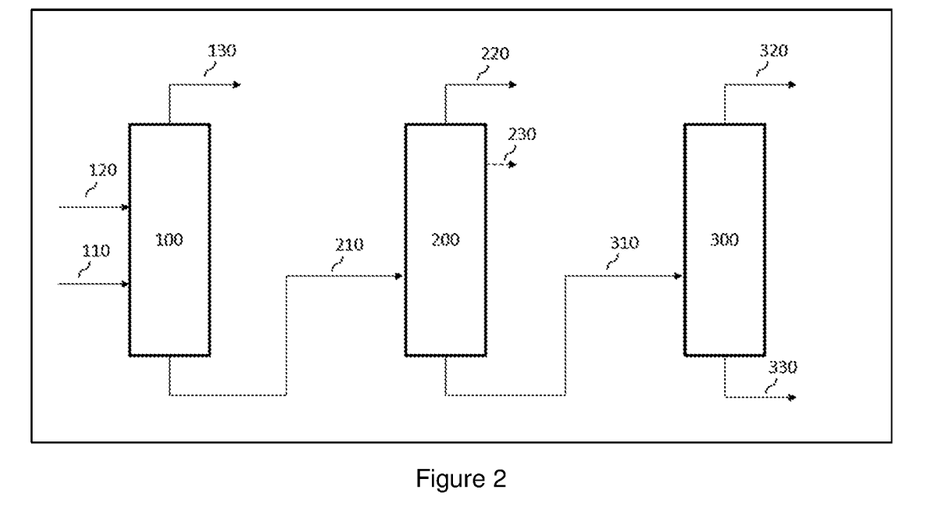
FIG. 2 illustrates a series of distillation columns and an azeotropic distillation column according to the present disclosure.

In one embodiment of the present invention, as shown in FIG. 2, the process has an azeotropic distillation column 100 with a feed stream 110 comprising acrylic acid, propionic acid, acetic acid, and high boiling compounds and a entrainer 120 consisting essentially of water with a product top stream 130 comprising the propionic acid, water, and other compounds forming a minimum boiling azeotrope with water and a product bottom stream 210 comprising acrylic acid and acetic acid. This product bottom stream 210 is sent to a second distillation column 200 to form a product top stream 220 comprising acetic acid and a product bottom stream 310 comprising acrylic acid and high boiling compounds with an optional side-draw stream 230 which is more concentrated in acetic acid than the product top stream 220. This product bottom stream 310 is sent to a third distillation column 300 to form a product top stream 320 comprising acrylic acid and a product bottom stream 330 comprising the remaining high boilers.

Figure 3:
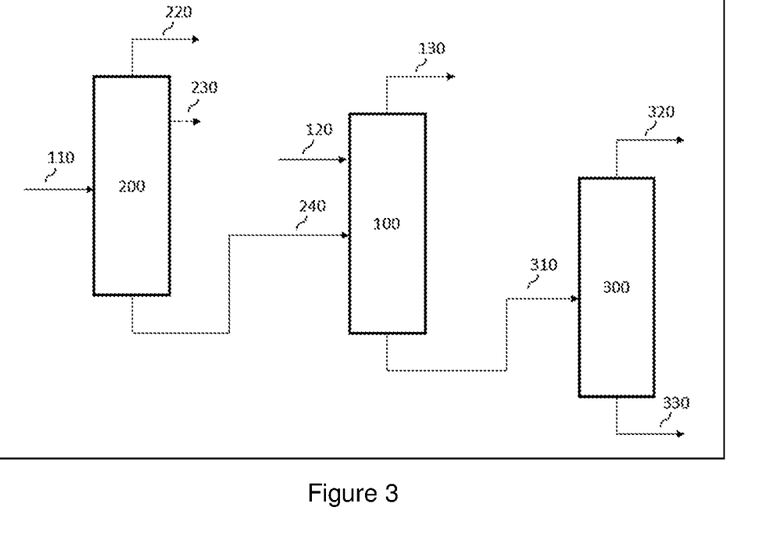
FIG. 3 illustrates a series of distillation columns and an azeotropic distillation column according to the present disclosure.

Another embodiment of the present invention, as shown in FIG. 3, the process has a first distillation column 200 with a feed stream 110 comprising acrylic acid, propionic acid, acetic acid, and high boiling compounds and a product top stream 220 comprising acetic acid and water and a product bottom stream 240 comprising acrylic acid and propionic acid with an optional product side-draw stream 230 which is more concentrated in acetic acid than the product top stream 220. The product bottom stream 240 is fed to an azeotropic distillation column 100 with an entrainer 120 consisting essentially of water with a product top stream 130 comprising water, propionic acid, and other compounds forming a minimum boiling azeotrope with water and a product bottom stream 310 comprising acrylic acid and high boilers. The product bottom stream 310 is fed to a third distillation column 300 with a product top stream 320 comprising acrylic acid and a product bottom stream 330 comprising high boilers.

Figure 4:
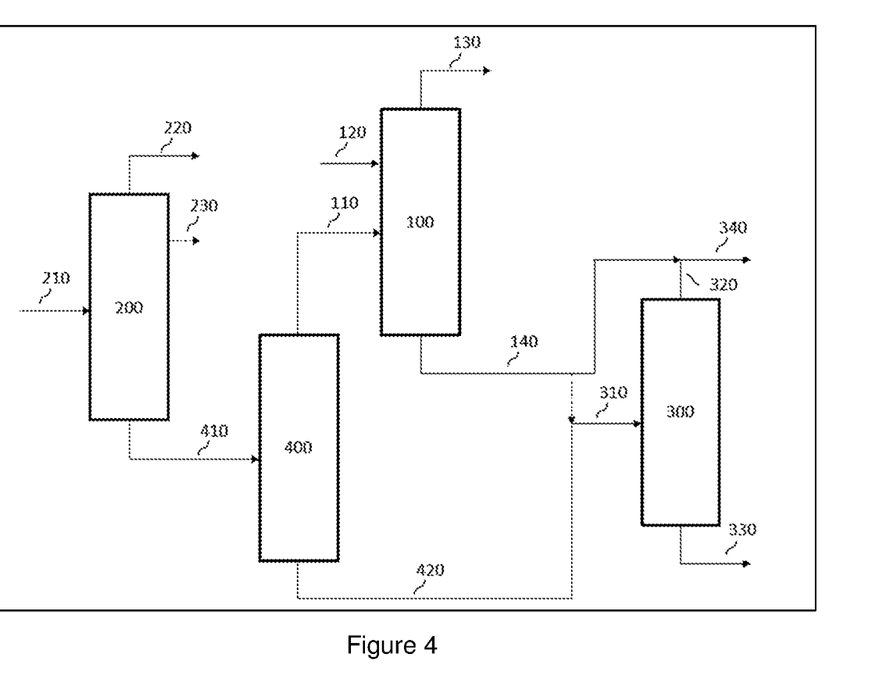
FIG. 4 illustrates a series of distillation columns and an azeotropic distillation column according to the present disclosure.

Another embodiment of the present invention, as shown in FIG. 4, the process has a first distillation column 200 with a feed stream 110 comprising acrylic acid, propionic acid, acetic acid, and high boiling compounds and a product top stream 220 comprising acetic acid and water and a product bottom stream 410 comprising acrylic acid and propionic acid with an optional product side-draw stream 230 which is more concentrated in acetic acid than the product top stream 220. The product bottom stream 410 is fed to a second distillation column 400 with a product top stream 430 comprising acrylic acid and propionic acid and a product bottom stream 420 comprising acrylic acid and high boiling compounds. The product top stream 430 is fed to an azeotropic distillation column 100 with an entrainer 120 consisting essentially water and a product top stream 130 comprising water, propionic acid, and other components forming minimum boiling azeotropes and a product bottom stream 140 comprising acrylic acid. The product bottom stream 420 is optionally combined with the product bottom stream 140 to form a feed stream 310 which is fed to a third distillation column 300 with a product top stream 320 comprising acrylic acid which is optionally combined with product bottom stream 140 and a product bottom stream 330 comprising high boiling components.

In one embodiment of the present disclosure, the feed stream 110 may contain greater than 50-80 wt % acetic acid, 5-35% acrylic acid, 0-40% water, and less than 3-5 wt % propionic acid. In another embodiment, the feed stream 110 may contain 50-80 wt % acetic acid, 5-35% acrylic acid, 0-40% water, and less than 1 wt % propionic acid. One aspect of the present disclosure is to separate the propionic acid from the desired acrylic acid product such that the acrylic acid product can meet propionic acid specifications for glacial acrylic acid.

Another embodiment of the present disclosure is to separate propionic acid from an acrylic acid stream to produce a less concentrated propionic acid acrylic acid stream. The feed stream 110 may be primarily acrylic acid comprising smaller concentrations of propionic acid, acetic acid, and other compounds which may or may not azeotrope with water. In one embodiment, the feed concentration could comprise 35-99.5 wt % acrylic acid, 0-60% water, less than 5% acetic acid, and less than 5% propionic acid. In one embodiment, the feed concentration could comprise 5-99.5 wt % acrylic acid, 1-60% water, less than 5% acetic acid, and less than 5% propionic acid.

One embodiment of the present invention, can be used to remove concentrated impurities in a purge stream from an acrylic acid purification process. For example, in melt crystallization there is a residue that is produced during the production of glacial acrylic acid. The residue is a concentrated impurity stream comprising acrylic acid dimers, acetic acid, propionic acid, furfural, acrylic acid, maleic acid, and other compounds. For example, if the impurity purge stream is treated to crack the acrylic acid dimers back to acrylic acid, the resulting product stream containing the volatile vapors can be sent to an azeotropic distillation column where the propionic acid, furfural, and any other compounds which azeotrope with water in the distillation column feed will be concentrated in the distillation column distillate product, whereas the acrylic acid, acetic acid, and other components not forming a minimum boiling azeotrope with water will concentrate in the column bottoms stream. This enables the separation of the close boiling propionic acid from the desired acrylic acid. Compounds which could be in the feed which form minimum boiling azeotropes with water may include furfural, benzaldehyde, and propionic acid.

Figure 5:
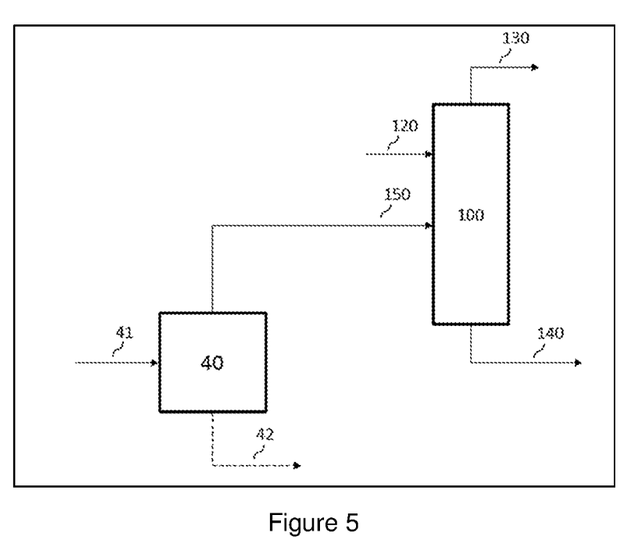
FIG. 5 illustrates a reactor and an azeotropic distillation column according to the present disclosure.

Another embodiment of the present invention, as shown in FIG. 5, the process has a feed stream 41 comprising acrylic acid, acrylic acid dimers and oligomers, acetic acid, and propionic acid that is fed to a reactor 40 where the acrylic acid dimers and oligomers are cracked back to acrylic acid with a high boiler purge bottom stream 42 and a top vapor stream 150 comprising acrylic acid and other components such as furfural, benzaldehyde, propionic acid, acetic acid, maleic acid, toluene, etc., that is fed to an azeotropic distillation column 100 with an entrainer 120 consisting essentially of water with a product top stream 130 comprising water, propionic acid, and other compounds forming minimum boiling azeotropes with water and a product bottom stream 140 comprising acrylic acid. In another embodiment of the present invention, the feed stream 41 comprises acrylic acid, acrylic acid oligomers, acetic acid, propionic acid, furfural, and maleic acid.

EXAMPLES

Aspen Plus V8.6 was used as the modeling software for all examples with an internally developed vapor-liquid equilibria (VLE) package was used as a basis for all models. Maleic acid is typically present in acrylic acid process streams. In these models, maleic acid represents high boiling components such as maleic acid, acrylic acid oligomers, and other components which do not form minimum boiling azeotropes with water. The resulting VLE at P=760 mmHg is shown in Table 1.

TABLE 1

Physical Property Information (Mass Fraction) (P = 760 mmHg)

| Boiling Point (° C.) | Formaldehyde | Water | Acetic Acid | Propionic Acid | Acrylic Acid | Maleic Acid | Furfural | Benzaldehyde |
|---|---|---|---|---|---|---|---|---|
| −19.5 | 1.00 | | | | | | | |
| 97.9 | | 0.68 | | | | | | 0.32 |
| 98.1 | | 0.66 | | | | | 0.34 | |
| 99.8 | | 0.79 | | 0.21 | | | | |
| 100.0 | | 1.00 | | | | | | |
| 118.0 | | | 1.00 | | | | | |
| 140.2 | | | | 0.63 | 0.37 | | | |
| 140.9 | | | | 1.00 | | | | |
| 142.0 | | | | | 1.00 | | | |
| 161.4 | | | | | | | 1.00 | |
| 178.9 | | | | | | | | 1.00 |
| 292.2 | | | | | | 1.00 | | |

Note—For all example tables, "trace" means<0.001 lb/hr. All other mass balance flow rates were rounded to the nearest 1 lb/hr.

Example #1A

Separation of Propionic Acid from Acrylic Acid Produced from the Reaction of Acetic Acid and Formaldehyde Column 100 (see FIG. 2) separates propionic acid from acrylic acid and acetic acid in this embodiment. This example demonstrates that the application of this concept can result in a final propionic acid concentration of 100 ppm in the purified acrylic acid product using the column inputs shown in Table 5 and feed compositions shown in Tables 1a and 2.

TABLE 1a

Example 1A-Stream Compositions (wt/wt %)

| Stream Component | 110 wt % | 120 wt % | 130 wt % | 210 wt % | 220 wt % | 230 wt % | 310 wt % | 320 wt % | 330 wt % |
|---|---|---|---|---|---|---|---|---|---|
| Water | 1.8% | 100.0% | 99.9% | 5.4% | 75.8% | 2.5% | <1 PPM | <1 PPM | <1 PPM |
| Acetic Acid | 72.7% | — | 106 PPM | 70.0% | 24.2% | 97.4% | 372 PPM | 471 PPM | <1 PPM |
| Acrylic Acid | 20.1% | — | 6 PPM | 19.4% | 10 PPM | 816 PPM | 78.9% | 99.8% | 356 PPM |
| Propionic Acid | 884 PPM | — | 580 PPM | 18 PPM | <1 PPM | <1 PPM | 74 PPM | 93 PPM | <1 PPM |
| Maleic Acid | 5.4% | — | <1 PPM | 5.2% | <1 PPM | <1 PPM | 21.1% | 0.2% | 100.0% |
| Formaldehyde | 57 PPM | — | 38 PPM | <1 PPM | <1 PPM | <1 PPM | <1 PPM | <1 PPM | <1 PPM |
| Total (lb/hr) | 52276 | 80000 | 78043 | 54233 | 2610 | 38350 | 13273 | 10491 | 2782 |

TABLE 2

Example 1A-Stream Mass Balance (lb/hr)

| Stream Component | 110 lb/hr | 120 lb/hr | 130 lb/hr | 210 lb/hr | 220 lb/hr | 230 lb/hr | 310 lb/hr | 320 lb/hr | 330 lb/hr |
|---|---|---|---|---|---|---|---|---|---|
| Water | 938 | 80000 | 77986 | 2952 | 1980 | 972 | trace | trace | trace |
| Acetic Acid | 37990 | — | 8 | 37982 | 631 | 37347 | 5 | 5 | trace |
| Acrylic Acid | 10499 | — | 0 | 10498 | 0 | 31 | 10467 | 10466 | 1 |
| Propionic Acid | 46 | — | 45 | 1 | trace | trace | 1 | 1 | trace |
| Maleic Acid | 2800 | — | trace | 2800 | trace | trace | 2800 | 19 | 2781 |
| Formaldehyde | 3 | — | 3 | trace | trace | trace | trace | trace | trace |
| Total (lb/hr) | 52276 | 80000 | 78043 | 54233 | 2610 | 38350 | 13273 | 10491 | 2782 |

TABLE 3

Modeling Inputs for Example 1A and 1B Column Simulations

| | Column | | |
|---|---|---|---|
| | 100 | 200 | 300 |
| Total Stages | 50 | 50 | 5 |
| Feed Stage | 28 | 25 | 3 |
| Entrainer Feed | 27 | — | — |
| RR (mass) | 15 | — | 0.01 |
| Boilup Ratio (mass) | — | 25 | — |
| D/F (mass) | 0.59 | — | — |
| B/F (mass) | — | 0.24 | 0.21 |
| Top Stage P (torr) | 1000 | 100 | 100 |
| Column P drop (torr) | 100 | 100 | 100 |

Example #1B

Separation of propionic acid from acrylic acid produced from the reaction of acetic acid and formaldehyde with additional impurities in the column feed (see FIG. 2).

This example shows that in addition to separating propionic acid, one embodiment will also separate other impurities from acrylic acid as long as they form minimum boiling azeotropes with water. Specifically, the feed in this example has furfural and benzaldehyde in addition to propionic acid. Furfural and benzaldehyde are two common impurities present in acrylic acid produced via the oxidation of propylene. This example demonstrates that the application of this embodiment can result in a purified acrylic acid product which can meet typical glacial acrylic acid product specifications.

TABLE 4

Example 1B-Stream Compositions (wt/wt %)

| Stream Component | 110 wt % | 120 wt % | 130 wt % | 210 wt % | 220 wt % | 230 wt % | 310 wt % | 320 wt % | 330 wt % |
|---|---|---|---|---|---|---|---|---|---|
| Water | 1.8% | 100.00% | 99.8% | 5.6% | 77.0% | 2.7% | <1 PPM | <1 PPM | <1 PPM |
| Acetic Acid | 72.5% | — | 105 PPM | 69.9% | 23.0% | 97.2% | 372 PPM | 471 PPM | <1 PPM |
| Acrylic Acid | 20.0% | — | 5 PPM | 19.3% | 10 PPM | 817 PPM | 78.9% | 99.8% | 356 PPM |
| Propionic Acid | 883 PPM | — | 579 PPM | 17 PPM | <1 PPM | <1 PPM | 72 PPM | 92 PPM | <1 PPM |
| Furfural | 0.1% | — | 669 PPM | <1 PPM | <1 PPM | <1 PPM | <1 PPM | <1 PPM | <1 PPM |
| Benzaldehyde | 0.1% | — | 669 PPM | <1 PPM | <1 PPM | <1 PPM | <1 PPM | <1 PPM | <1 PPM |
| Maleic Acid | 5.3% | — | <1 PPM | 5.2% | <1 PPM | <1 PPM | 21.1% | 0.2% | 100.0% |
| Formaldehyde | 57 PPM | — | 38 PPM | <1 PPM | <1 PPM | <1 PPM | <1 PPM | <1 PPM | <1 PPM |
| Total (lb/hr) | 52276 | 80000 | 78043 | 54233 | 2618 | 38369 | 13246 | 10470 | 2776 |

TABLE 5

Example 1B-Stream Mass Balance (lb/hr)

| Stream Component | 110 lb/hr | 120 lb/hr | 130 lb/hr | 210 lb/hr | 220 lb/hr | 230 lb/hr | 310 lb/hr | 320 lb/hr | 330 lb/hr |
|---|---|---|---|---|---|---|---|---|---|
| Water | 936 | 80000 | 77882 | 3054 | 2017 | 1038 | trace | trace | trace |
| Acetic Acid | 37915 | — | 8 | 37906 | 601 | 37300 | 5 | 5 | trace |
| Acrylic Acid | 10478 | — | 0 | 10477 | 0 | 31 | 10446 | 10445 | 1 |
| Propionic Acid | 46 | — | 45 | 1 | trace | trace | 1 | 1 | trace |
| Furfural | 52 | — | 52 | trace | trace | trace | trace | trace | trace |
| Benzaldehyde | 52 | — | 52 | trace | trace | trace | trace | trace | trace |
| Maleic Acid | 2794 | — | trace | 2794 | trace | trace | 2794 | 19 | 2775 |
| Formaldehyde | 3 | — | 3 | trace | trace | trace | trace | trace | trace |
| Total (lb/hr) | 52276 | 80000 | 78043 | 54233 | 2618 | 38369 | 13246 | 10470 | 2776 |

Example #2

Separation of Propionic Acid from Acrylic Acid with a Feed Less Concentrated in Acetic Acid This is a column sequence, where in one embodiment column 100 (see FIG. 4) is separating propionic acid from acrylic acid using water as an entrainer. However, the acetic acid and water in the feed are separated initially in column 200. Column 400 is a pre-fractionation column providing a non-sharp split of acrylic acid from propionic acid. Column 300 separates acrylic acid from high boilers (HBs) like maleic acid. This example demonstrates another column sequence with a different azeotropic column feed composition which can result in a final propionic acid concentration of less than 100 ppm in the purified acrylic acid product (combining stream 140 and stream 320) using the column inputs shown in Table 8 and feed compositions shown in Tables 6 and 7.

Example #3A

Separation of Propionic Acid and Furfural from A Purge Stream from an Acrylic Acid Purification Process In this embodiment, the column feed contains other components that can azeotrope with water such as furfural. FIG. 5 shows the general concept with Tables 9, 10, and 11 showing the model details and results. This example demonstrates that this concept can be used to separate other components that azeotrope with water, such as furfural, along with propionic acid from a typical feed from an acrylic acid process purge stream.

TABLE 6

Example 2-Stream Compositions (wt/wt %)

| Component | 110 wt % | 220 wt % | 410 wt % | 430 wt % | 420/310 wt % | 120 wt % | 130 wt % | 140 wt % | 320 wt % | 330 wt % |
|---|---|---|---|---|---|---|---|---|---|---|
| Water | 1.8% | 2.4% | <1 PPM | <1 PPM | <1 PPM | 100.0% | 98.2% | <1 PPM | <1 PPM | <1 PPM |
| Acetic Acid | 72.7% | 97.5% | <1 PPM | <1 PPM | <1 PPM | — | <1 PPM | <1 PPM | <1 PPM | <1 PPM |
| Acrylic Acid | 20.1% | 368 PPM | 78.7% | 99.3% | 58.9% | — | 1.7% | 100.0% | 99.5% | 106 PPM |
| Propionic Acid | 884 PPM | <1 PPM | 0.3% | 0.7% | 68 PPM | — | 0.2% | 76 PPM | 115 PPM | <1 PPM |
| Maleic Acid | 5.4% | <1 PPM | 21.0% | <1 PPM | 41.1% | — | <1 PPM | <1 PPM | 0.5% | 100.0% |
| Formaldehyde | 57 PPM | 77 PPM | <1 PPM | <1 PPM | <1 PPM | — | <1 PPM | <1 PPM | <1 PPM | <1 PPM |
| Total (lb/hr) | 52276 | 38946 | 13330 | 6514 | 6816 | 25000 | 25469 | 6045 | 4037 | 2780 |

TABLE 7

Example 2-Stream Mass Balance (lb/hr)

| Component | 110 lb/hr | 220 lb/hr | 410 lb/hr | 430 lb/hr | 420/310 lb/hr | 120 lb/hr | 130 lb/hr | 140 lb/hr | 320 lb/hr | 330 lb/hr |
|---|---|---|---|---|---|---|---|---|---|---|
| Water | 938 | 938 | trace | trace | trace | 25000 | 25000 | trace | trace | trace |
| Acetic Acid | 37990 | 37990 | trace | trace | trace | — | trace | trace | trace | trace |
| Acrylic Acid | 10499 | 14 | 10485 | 6468 | 4016 | — | 424 | 6045 | 4016 | 0 |
| Propionic Acid | 46 | 0 | 46 | 46 | 0 | — | 45 | 0 | 0 | trace |
| Maleic Acid | 2800 | trace | 2800 | trace | 2800 | — | trace | trace | 20 | 2780 |
| Formaldehyde | 3 | 3 | trace | trace | trace | — | trace | trace | trace | trace |
| Total (lb/hr) | 52276 | 38946 | 13330 | 6514 | 6816 | 25000 | 25469 | 6045 | 4037 | 2780 |

TABLE 8

Modeling Inputs for Example 2 Column Simulations

| | Column | | | |
|---|---|---|---|---|
| | 1 | 2 | 3 | 4 |
| Total Stages | 50 | 50 | 50 | 5 |
| Feed Stage | 28 | 10 | 11 | 3 |
| Entrainer Feed | — | — | 10 | — |
| RR (mass) | 15 | 10 | 10.00 | 0.01 |
| Boilup Ratio (mass) | — | — | — | — |
| D/F (mass) | — | 0.3 | 0.74 | — |
| B/F (mass) | 0.255 | — | — | 0.41 |
| Top Stage P (torr) | 100 | 100 | 100 | 100 |
| Column P drop (torr) | 100 | 100 | 100 | 100 |

TABLE 9

Example 3A - Stream Compositions (wt/wt %)

| Component | 150 wt % | 120 wt % | 130 wt % | 140 wt % |
|---|---|---|---|---|
| Water | <1 PPM | 100.0% | 69.8% | 32.2% |
| Acetic Acid | 7.8% | — | 15 PPM | 12.0% |
| Acrylic Acid | 11.3% | — | 2 PPM | 17.4% |
| Propionic Acid | 17.1% | — | 9.2% | 0.1% |
| Furfural | 38.9% | — | 21.0% | trace |
| Maleic Acid | 24.9% | — | trace | 38.3% |
| Total (lb/hr) | 10000 | 15000 | 18500 | 6500 |

TABLE 10

Example 3A - Stream Mass Balance (lb/hr)

| Component | 150 lb/hr | 120 lb/hr | 130 lb/hr | 140 lb/hr |
|---|---|---|---|---|
| Water | trace | 15000 | 12907 | 2093 |
| Acetic Acid | 780 | — | 0 | 780 |
| Acrylic Acid | 1130 | — | 0 | 1130 |
| Propionic Acid | 1710 | — | 1703 | 7 |
| Furfural | 3890 | — | 3890 | trace |
| Maleic Acid | 2490 | — | trace | 2490 |
| Total (lb/hr) | 10000 | 15000 | 18500 | 6500 |

TABLE 11

Modeling Inputs for 3A Column Simulations

| Column | 1 |
|---|---|
| Total Stages | 50 |
| Feed Stage | 25 |
| Entrainer Feed | 24 |
| RR (mass) | 10 |
| Boilup Ratio (mass) | — |
| D/F (mass) | 0.74 |
| B/F (mass) | — |
| Top Stage P (psia) | 14.7 |
| Column P drop (torr) | 100 |

Example 3B

This is another embodiment, where the column feed contains additional components that can azeotrope with water. In this case it is furfural and benzaldehyde. FIG. 5 shows the general concept with Tables 12, 13, and 14 showing the model details and results. This example demonstrates that this concept can be used to separate multiple components that azeotrope with water, such as furfural and benzaldehyde, along with propionic acid from a typical feed from an acrylic acid process purge stream.

TABLE 12

Example 3B - Stream Compositions (wt/wt %)

| Component | 150 wt % | 120 wt % | 130 wt % | 140 wt % |
|---|---|---|---|---|
| Water | <1 PPM | 100.0% | 73.9% | 48.8% |
| Acetic Acid | 7.8% | — | 15 PPM | 9.1% |
| Acrylic Acid | 11.3% | — | 4 PPM | 13.1% |
| Propionic Acid | 17.1% | — | 8.0% | 676 PPM |
| Furfural | 19.5% | — | 9.1% | <1 PPM |
| Benzaldehyde | 19.5% | — | 9.1% | <1 PPM |
| Maleic Acid | 24.9% | — | <1 PPM | 29.0% |
| Total (lb/hr) | 10000 | 20000 | 21400 | 8600 |

TABLE 13

Example 3B - Stream Mass Balance (lb/hr)

| Component | 150 lb/hr | 120 lb/hr | 130 lb/hr | 140 lb/hr |
|---|---|---|---|---|
| Water | trace | 20000 | 15805 | 4195 |
| Acetic Acid | 780 | — | 0 | 780 |
| Acrylic Acid | 1130 | — | 0 | 1130 |
| Propionic Acid | 1710 | — | 1704 | 6 |
| Furfural | 1945 | — | 1945 | trace |
| Benzaldehyde | 1945 | — | 1945 | trace |
| Maleic Acid | 2490 | — | trace | 2490 |
| Total (lb/hr) | 10000 | 20000 | 21400 | 8600 |

TABLE 14

Modeling Inputs for 3B Column Simulations

| Column | 1 |
|---|---|
| Total Stages | 50 |
| Feed Stage | 25 |
| Entrainer Feed | 24 |
| RR (mass) | 10.4 |
| Boilup Ratio (mass) | — |
| D/F (mass) | 0.71 |
| B/F (mass) | — |
| Top Stage P (psia) | 14.7 |
| Column P drop (torr) | 100 |

We claim:

1. A process comprising:
   supplying a feed stream to an azeotropic distillation column, wherein the feed stream comprises acrylic acid, and at least one saturated organic acid with 3 or more carbon atoms;
   adding water as an entrainer to the azeotropic distillation column; and
   controlling the column at a temperature and pressure such that the feed stream is separated into at least a product top stream and a product bottom stream, wherein the product top stream comprises the saturated organic acid and water and wherein the product bottom stream comprises the acrylic acid and optionally acetic acid.

2. A process comprising:
   supplying a feed stream to an azeotropic distillation column, wherein the feed stream comprises acrylic acid, and propionic acid;
   adding water as an entrainer to in the azeotropic distillation column; and
   controlling the column at a temperature and pressure such that the feed stream is separated into at least a product top stream and a product bottom stream, wherein the product top stream comprises propionic acid and water and wherein the product bottom stream comprises the acrylic acid.

3. A process comprising:
   supplying a first feed stream to a first azeotropic distillation column, wherein the first feed stream comprises acrylic acid, propionic acid, acetic acid, and high boiling compounds;
   adding water an entrainer to the azeotropic distillation column;
   controlling the column at a temperature and pressure such that the first feed stream is separated into at least a first product top stream and a first product bottom stream, wherein the first product top stream comprises propionic acid, water and other compounds forming a minimum boiling azeotrope with water and wherein the first product bottom stream comprises the acrylic acid and acetic acid;
   feeding the first product bottom stream of water, acrylic acid and acetic acid into a second distillation column to form a second top product stream comprising water and acetic acid and a second product bottom stream comprising acrylic acid and high boiling compounds with an optional second product side stream comprising concentrated acetic acid; and feeding the second product bottom stream of acrylic acid and high boiling compounds into a third distillation column to form a third product top stream comprising acrylic acid and a third product bottom stream comprising the remaining high boiling compounds.

4. A process comprising:

supplying a first feed stream to a first distillation column, wherein the first feed stream comprises acrylic acid, propionic acid, acetic acid, and high boiling compounds to form a first product top stream comprising acetic acid and a first product bottom stream comprising acrylic acid and propionic acid with an optional product side stream comprising concentrated acetic acid;

feeding said first product bottom stream comprising acrylic acid and propionic acid into an azeotropic distillation column, adding water as an entrainer to the azeotropic distillation column, controlling the column at a temperature and pressure such that the second feed stream is separated into at least a second product top stream and a second product bottom stream, wherein the second product top stream comprises water, propionic acid, and other compounds forming a minimum boiling azeotrope with water and wherein the second product bottom stream comprises the acrylic acid and high boiling compounds; and feeding the second product bottom stream of acrylic acid and high boiling compounds into a second distillation column to form a third top product stream comprising acrylic acid and a third product bottom stream comprising high boiling compounds.

5. A process comprising:

supplying a first feed stream to a first distillation column, wherein the first feed stream comprises acrylic acid, propionic acid, acetic acid, and high boiling compounds to form a first product top stream comprising acetic acid and a first product bottom stream comprising acrylic acid and propionic acid with an optional product side stream comprising concentrated acetic acid;

feeding said first product bottom stream comprising acrylic acid and propionic acid into a second distillation column, such that the second feed stream is separated into at least a second product top stream and a second product bottom stream, wherein the second product top stream comprises acrylic acid and propionic acid and wherein the second product bottom stream comprises the acrylic acid and high boiling compounds;

feeding said second product top stream comprising acrylic acid and propionic acid into an azeotropic distillation column, and adding water as an entrainer to the azeotropic distillation column, controlling the column at a temperature and pressure such that the feed stream is separated into at least a third product top stream and a third product bottom stream, wherein the third product top stream comprises water, propionic acid, and other compounds forming a minimum boiling azeotrope with water and wherein the third product bottom stream comprises the acrylic acid and high boiling compounds; and feeding said second product bottom stream of acrylic acid and high boiling compounds into a third distillation column to form a fourth product top product stream comprising acrylic acid and a fourth product bottom stream comprising high boiling compounds.

6. The process of claim 5, wherein the process further comprises combining the third product bottom stream of acrylic acid and high boiling compounds with the second product bottom stream of acrylic acid and high boiling compounds and feeding this combined stream into a third distillation column to form a fourth product top product stream comprising acrylic acid which can be optionally combined with the acrylic acid from the second product bottom stream and a fourth product bottom stream comprising high boiling compounds.

7. A process comprising:

supplying a first feed stream to a reactor, wherein the first feed stream comprises acrylic acid, acrylic acid oligomers, acetic acid, and propionic acid, wherein the acrylic acid oligomers and the feed stream is heated and cracked back to acrylic acid; and feeding the cracked vapor stream from the reactor to a first azeotropic distillation column and adding water as an entrainer to form a product top stream comprising water, propionic acid, and other compounds forming minimum boiling azeotropes with water and a product bottom stream comprising acrylic acid.

8. A process comprising:

supplying a first feed stream to a reactor, wherein the first feed stream comprises acrylic acid, acrylic acid oligomers, acetic acid, propionic acid, furfural, and maleic acid and the feed stream is heated and cracked back to acrylic acid; and feeding the cracked vapor stream from the reactor to a first azeotropic distillation column and adding water as an entrainer to form a product top stream comprising water, propionic acid, furfural and other compounds forming minimum boiling azeotropes with water and a product bottom stream comprising acrylic acid.

9. A process according to claim 1, wherein the feed stream is recovered from the production of acrylic acid by propylene oxidation, said feed stream comprising acrylic acid, acetic acid, propionic acid, and high boiling by-products.

10. A process according to claim 1, wherein the feed stream is recovered from the production of acrylic acid by an aldolization reaction including the reaction between acetic acid and formaldehyde, said feed stream comprising acrylic acid, acetic acid, propionic acid, and high boiling by-products.

11. A process according to claim 1, wherein the feed stream is recovered from the production of acrylic acid from alternative or bio-based reactions including propane oxidation, 3-hydroxypropionic acid, glycerol, and lactic acid, said feed stream comprising acrylic acid, acetic acid, propionic acid, and high boiling by-products.

12. A process according to any one of claim 1 or 2, wherein the product top stream from the azeotropic distillation column further comprises other organic compounds forming minimum boiling azeotropes with water such as furfural, benzaldehyde, and toluene.

13. A process according to any one of claim 1 or 2, wherein the product top stream from the azeotropic distillation column contains at least 90% of the propionic acid in the product feed stream.

14. A process according to any one of claim 1 or 2, wherein the acrylic acid is present in the product bottom stream from the azeotropic distillation column is a higher concentration than in the feed stream.

15. A process according to claim 1, wherein the azeotropic distillation column operates at a pressure less than or equal to 1000 torr.

16. A process according to claim 1, wherein the azeotropic distillation column operates at a temperature less than 140° C. where the concentration of acrylic acid is greater than 35 wt %.

17. A process according to claim 1, wherein the azeotropic distillation column operates at a temperature less than 115° C. where the concentration of acrylic acid is greater than 35 wt %.

18. A process according to claim 1, wherein the water feed ratio in the azeotropic distillation column is greater than 1.0.

19. A process according to claim 1, wherein the water feed ratio in the azeotropic distillation column is 1.4.

20. A process according to claim 1, wherein the product stream comprising high purity acrylic acid has less than 500 ppm acetic acid and less than 100 ppm propionic acid.

\* \* \* \* \*

UNITED STATES PATENT AND TRADEMARK OFFICE
CERTIFICATE OF CORRECTION

| | | |
|---|---|---|
| PATENT NO. | : 10,968,160 B2 | Page 1 of 1 |
| APPLICATION NO. | : 16/471214 | |
| DATED | : April 6, 2021 | |
| INVENTOR(S) | : Craig Alan Hoyme et al. | |

It is certified that error appears in the above-identified patent and that said Letters Patent is hereby corrected as shown below:

In the Specification

Column 15, Table 6, Column Header 2, please replace "110" with --210--.

Column 15, Table 6, Column Header 5, please replace "430" with --110--.

Column 15, Table 7, Column Header 2, please replace "110" with --210--.

Column 15, Table 7, Column Header 5, please replace "430" with --110--.

Signed and Sealed this
Ninth Day of May, 2023

Katherine Kelly Vidal
*Director of the United States Patent and Trademark Office*